United States Patent
Suzuki et al.

(10) Patent No.: US 9,012,632 B2
(45) Date of Patent: Apr. 21, 2015

(54) METHOD FOR RAPIDLY METHYLATING HETEROAROMATIC ARENE AND METHOD FOR PRODUCING TRACER FOR USE IN PET

(75) Inventors: Masaaki Suzuki, Koube (JP); Hisashi Doi, Koube (JP); Hiroko Koyama, Gifu (JP)

(73) Assignee: Riken, Wako-Shi (JP)

( * ) Notice: Subject to any disclaimer, the term of this patent is extended or adjusted under 35 U.S.C. 154(b) by 42 days.

(21) Appl. No.: 13/142,207

(22) PCT Filed: Dec. 25, 2009

(86) PCT No.: PCT/JP2009/071694
§ 371 (c)(1),
(2), (4) Date: Jun. 24, 2011

(87) PCT Pub. No.: WO2010/074272
PCT Pub. Date: Jul. 1, 2010

(65) Prior Publication Data
US 2011/0263849 A1 Oct. 27, 2011

(30) Foreign Application Priority Data
Dec. 26, 2008 (JP) .................................. 2008-335250

(51) Int. Cl.
C07D 221/00 (2006.01)
C07D 217/02 (2006.01)
C07D 333/08 (2006.01)
C07D 307/36 (2006.01)
C07D 231/12 (2006.01)
C07D 237/08 (2006.01)
C07D 239/26 (2006.01)
C07D 213/127 (2006.01)

(52) U.S. Cl.
CPC .......... *C07D 213/127* (2013.01); *C07D 217/02* (2013.01); *C07D 231/12* (2013.01); *C07D 237/08* (2013.01); *C07D 239/26* (2013.01); *C07D 307/36* (2013.01); *C07D 333/08* (2013.01)

(58) Field of Classification Search
USPC .......... 546/349, 139; 549/86, 506; 548/373.1; 544/242, 224
See application file for complete search history.

(56) References Cited

U.S. PATENT DOCUMENTS

2009/0238759 A1  9/2009  Suzuki et al.
2010/0249477 A1  9/2010  Suzuki et al.
2012/0263646 A1* 10/2012  Catoen et al. ............... 424/1.89

FOREIGN PATENT DOCUMENTS

| EP | 1 947 074 A1 | 7/2008 |
| JP | 2006-076891 A | 3/2006 |
| WO | WO 2007/046258 A1 | 4/2007 |
| WO | WO 2008/023780 A1 | 2/2008 |

OTHER PUBLICATIONS

Maes, et al., Chem. Soc. Rev., 2008, 37, 2393-2402.*
Vida, et al., Photochem. Photobiol. Sci., 2012, 11, 1645-1651.*
Andersson et al., Palladium-promoted Coupling Reactions of [11C]Methyl Iodide with Organotin and Organoboron Compounds, Acta Chemica Scandinavica, vol. 49, 1995, pp. 683-688, XP002673891.
Bourdier et al., Synthesis and Biological Evaluation of N-Substituted Quinolinimides, as Potential Ligands for in Vivo Imaging Studies of •- Opioid Receptors, Bioconjugate Chemistry, vol. 18, No. 2, Mar. 7, 2007, pp. 538-548, XP002673888.
Bourdier et al., Tetra- and Monoorganotin Reagents in Palladium-Mediated Cross-Coupling Reactions for the Labeling with Carbon-11 of PET Tracers, No. 6, 2008, pp. 978-984, XP002673887.
Karimi et al., Synthesis of 3-[(2S)-azetidin-2-ylmethoxy]-5[11C]-methylpyridine, an analogue of A-85380, via a Stille coupling, Journal of Labelled Compounds and Radiopharmaceuticals, vol. 45, Apr. 2002, pp. 423-434, XP002673889.
Kim et al., 2-Substitution of Adenine Nucleotide Analogues Containing a Bicyclo[3.1.0]hexane Ring System Locked in a Northern Conformation:• Enhanced Potency as P2Y1 Receptor Antagonists, Journal of Medicinal Chemistry, vol. 46, No. 23, Oct. 14, 2003, pp. 4974-4987, XP002388426.
Mee et al., Significant Enhancement of the Stille Reaction with a New Combination of Reagents—Copper(I) Iodide with Cesium Fluoride, Chemistry—A European Journal, vol. 11, No. 11, May 20, 2005, pp. 3294-3308, XP003012120.
Supplementary European Search Report dated Jun. 12, 2012 in European Application No. EP09835068.9.
Suzuki et al., Pd0-Mediated Rapid Coupling between Methyl Iodide and Heteroarylstannanes: An Efficient and General Method for the Incorporation of a Positron-Emitting 11C Radionuclide into Heteroaromatic Frameworks, Chemistry—A European Journal, vol. 15, Nov. 16, 2009, pp. 12489-12495, XP002673892.
Bao et al., "Exploration of the Stille Coupling Reaction for the Syntheses of Functional Polymers", Journal of the American Chemical Society, vol. 117, No. 50, pp. 12426-12435, 1995.

(Continued)

*Primary Examiner* — James O Wilson
*Assistant Examiner* — Cecilia M Jaisle
(74) *Attorney, Agent, or Firm* — Birch, Stewart, Kolasch & Birch, LLP

(57) ABSTRACT

Provided is a method whereby a heteroaromatic ring aryl can be very rapidly methylated at a high yield. In an N-alkyl-2-pyrrolidinone, a heteroaromatic ring aryltrialkylstannan is cross-coupled with methyl iodide in the presence of a palladium complex, a phosphine ligand, a cuprous halide, a carbonic acid salt and/or an alkali metal fluoride to thereby rapidly methylate the heteroaromatic ring aryl. (Formula shows a case wherein the heteroaromatic ring aryl is a pyridyl group.)

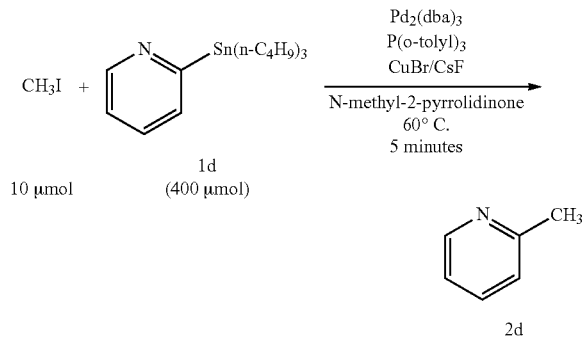

10 Claims, 1 Drawing Sheet

(56) References Cited

OTHER PUBLICATIONS

Bennacef et al., "Functionalization through Lithiation of (S)-N-(1-Phenylpropyl)-2-phenylquinoline-4-carboxamide. Application to the Labeling with Carbon-11 of NK-3 Receptor Antagonist SB 222200", J. Org. Chem., vol. 72, pp. 2161-2165, 2007.

Farina, et al., "Large Rate Accelerations in the Stille Reaction with Tri-2-furylphosphine and Triphenylarsine as Palladium Ligands: Mechanistic and Synthetic Implications", Journal of the American Chemical Society, vol. 113, No. 25, pp. 9585-9595, 1991.

Hosoya et al., "Rapid methylation of terminal acetylenes by the Stille coupling of methyl iodide with alkynyltributylstannanes: a general protocol potentially useful for the synthesis of short-lived 11CH3-labeled PET tracers with a 1-propynyl group", Org. Biomol. Chem., vol. 2, pp. 24-27, 2004.

Hosoya et al., "Rapid methylation on carbon frameworks useful for the synthesis of 11CH3-incorporated PET tracers: Pd(0)-mediated rapid coupling of methyl iodide with an alkenyltributylstannane leading to a 1-methylalkene", Org. Biomol. Chem., vol. 4, pp. 410-415, 2006.

Huang et al., "A Positron Emission Tomography Radioligand for the in Vivo Labeling of Metabotropic Glutamate 1 Receptor: (3-Ethyl-2-[11C]methyl-6-quinolinyl)(cis-4-methoxycyclohexyl)methanone", J. Med. Chem., vol. 48, pp. 5096-5099, 2005.

Iida et al., "Evaluation of 5-11C-Methyl-A-85380 as an Imaging Agent for PET Investigations of Brain Nicotinic Acetylcholine Receptors", The Journal of Nuclear Medicine, vol. 45, No. 5, pp. 878-884, May 2004.

Mee et al., "Stille Coupling Mde Easier—The Synergic Effect of Copper(I) Salts and Fluoride Ion", Angewandte Chem. International Edition., vol. 43, pp. 1132-1136, 2004.

Menzel et al., "Room-Temperature Stille Cross-Coupling of Alkenyltin Reagents and Functionalized Alkyl Bromides that Possess B Hydrogens", J. Am. Chem. Soc., vol. 125, pp. 3718-3719, 2003.

Prabhakaran et al., "Synthesis of [11C]celecoxib: a potential PET probe for imaging COX-2 expression", Journal of Labelled Compounds and Radiopharmaceuticals, vol. 48, pp. 887-895, 2005.

Ryoji Noyori, "Asymmetric Catalysis: Science and Opportunities (Nobel Lecture)", Angew. Chem. Int. Ed. vol. 41, pp. 2008-2022, 2002.

Sandell et al., "Synthesis, Radiolabelling and Preliminary Biological Evaluation of Radiolabeled 5-Methyl-6-nitroquipazine, a Potential Radioligand for the Serotonin Transporter", Bioorganic & Medicinal Chemistry Letters, vol. 12, pp. 3611-3613, 2002.

Suzuki et al., "Rapid methylation on carbon frameworks leading to the synthesis of a PET tracer capable of imaging a novel CNS-type prostacyclin receptor in living human brain", Trends in Analytical Chemistry, vol. 23, No. 8, pp. 595-607, 2004.

Suzuki et al., "Molecular Design of Prostaglandin Probes in Brain Research: High, specific Binding to a Novel Prostacyclin Receptor in the Central Nervous System", Bull. Chem. Soc. Jpn., vol. 73, pp. 1053-1070, 2000.

Suzuki et al., "Rapid Coupling of Methyl Iodide with Aryltributylstannanes Mediated by Palladium(0) Complexes: A General Protocol for the Synthesis of 11CH3-Labeled PET Tracers", Chem. Eur. J., vol. 3, No. 12, pp. 2039-2042, 1997.

Tang et al., "Ligands for Palladium-Catalyzed Cross-Couplings of Alkyl Halides: Use of an Alkyldiaminophosphane Expands the Scope of the Stille Reaction", Angew. Chem. Int. Ed., vol. 42, pp. 5079-5082, 2003.

Tarkiainen et al., "Carbon-11 labelling of MADAM in two different positions: a highly selective PET radioligand for the serotonin transporter", Journal of Labelled Compounds and Radiopharmaceuticals, vol. 44, pp. 1013-1023, 2001.

\* cited by examiner

FIG. 4

RESULTS OF SYNTHESIS OF $^{11}$C-LABELED 3-PICOLINE AND 2-PICOLINE

| | STARTING MATERIAL | Cu (I) X/BASE | TEMPERATURE | PRODUCT, HPLC ANALYTICAL YIELD, ANALYTICAL CONDITIONS |
|---|---|---|---|---|
| EXAMPLE 4 | 3-Sn(n-C$_4$H$_9$)$_3$ pyridine | Cu(I)Br/CsF | 60°C | 3-$^{11}$CH$_3$ pyridine, 91.4%, MS-II 4.6 × 150 mm, 30 °C, CH$_3$CN:H$_2$O = 25:75, 1 mL/min |
| EXAMPLE 5 | 3-Sn(n-C$_4$H$_9$)$_3$ pyridine | Cu(I)Cl/K$_2$CO$_3$ | 60°C | 3-$^{11}$CH$_3$ pyridine, 91.3%, MS-II 4.6 × 150 mm, 30 °C, CH$_3$CN:H$_2$O = 25:75, 1 mL/min |
| EXAMPLE 6 | 2-Sn(n-C$_4$H$_9$)$_3$ pyridine | Cu(I)Cl/K$_2$CO$_3$ | 60°C | 2-$^{11}$CH$_3$ pyridine, 98.9%, MS-II 4.6 × 150 mm, 30 °C, CH$_3$CN:H$_2$O = 20:80, 1 mL/min |

METHOD FOR RAPIDLY METHYLATING HETEROAROMATIC ARENE AND METHOD FOR PRODUCING TRACER FOR USE IN PET

TECHNICAL FIELD

The present invention relates to a method for rapidly methylating a heteroaromatic arene by cross-coupling methyl iodide with a heteroaromatic aryltrialkylstannane in a short time and to a PET tracer preparation kit using the method. The invention is suitable for use in methods for producing tracers to be used in positron emission tomography (hereinafter referred to as "PET").

BACKGROUND ART

PET is a method that includes administering, into a living body, a compound labeled with a positron-emitting, short-lived radionuclide, measuring gamma rays generated by the labeled compound (hereinafter referred to as "tracer") with a PET camera (a detector comprising a gamma ray scintillator and a photomultiplier), and imaging the body distribution of the labeled compound. PET is used in a nuclear medicine examination method to identify tumor sites such as cancer cells, diagnosis of Alzheimer disease, brain infarction, etc., diagnosis of mental disorders such as depression, treatment evaluation, pharmacokinetic evaluation, and drug efficacy evaluation.

PET is performed using a tracer labeled with a short-lived radionuclide such as $^{11}$C or $^{18}$F. In particular, $^{11}$C, labeled tracers have many advantages as described below.

(1) The application range of $^{11}$C-labeled tracers is very wide, because the carbon atom to be used exists in all organic compounds.

(2) Precursor compounds such as $^{11}$CH$_3$I, $^{11}$CO, and $^{11}$CO$_2$ for use in the synthesis of $^{11}$C-labeled tracers are prepared by well-established methods, and purified precursors are constantly available.

(3) Since $^{11}$C-containing tracers have a short half-life (20.3 minutes), many trial experiments for fundamental researches or many clinical tests can be performed in a day, and there is no need to pay special attention to the treatment of radiolabeled by-products generated after the synthesis reaction.

Therefore, $^{11}$C-labeled tracers can be considered to be the most ideal tracers for use in PET. However, since $^{11}$C has a very short half-life of 20 minutes, the process including the start of reaction, purification of the product, and administration has to be performed within 40 minutes. Therefore, the reaction for the synthesis of the tracers has to be completed within about 5 to 10 minutes. Methods for performing such rapid reaction in high yield have not been established yet, and this provides a problem when $^{11}$C-labeled tracers are used in PET.

Methods for synthesizing PET tracers using $^{11}$C as a radionuclide include methods of bonding a $^{11}$C-labeled methyl group to a hetero atom such as O, S, or N; and methods of bonding a $^{11}$C-labeled methyl group to a carbon atom of a carbon skeleton. Tracers having a $^{11}$C-labeled methyl group bonded to a hetero atom such as O, S, or N are often quickly converted into other compounds through metabolism. Therefore, such tracers have the disadvantage that when clinically used, such tracers are changed until they reach the target organ, so that proper diagnosis or treatment may be impossible. Such tracers are also not suitable as means for searching candidate compounds for drug development, because the methylated compounds may exhibit biological activity completely different from that of the compounds before the methylation.

In contrast, tracers having $^{11}$C methyl bonded to a carbon atom of a carbon skeleton have advantages as described below. (1) The methyl group is a sterically smallest, non-polar functional group and therefore has a minimum effect on the biological activity of parent compounds after it is introduced, which provides a high degree of freedom for molecular design and is suitable for candidate compound screening for drug development. (2) C-methylated products are more stable in metabolic processes than O- or N-methylated products and therefore allow production of highly reliable images and proper diagnosis or treatment of diseases.

Under the circumstances, the inventors have developed a method for rapidly methylating in which methyl iodide and an organotin compound are subjected to Stille coupling reaction, which has received attention (Non-Patent Document 1). This method enables cross-coupling between $sp^2$-$sp^3$ carbon atoms, which has been considered to be difficult for conventional Stille coupling reactions. For example, methylation proceeds in a yield of 90% or more when methyl iodide, an excess of tributylphenylstannane, tri-o-tolylphosphine, and unsaturated palladium are allowed to react in a DMF solvent at 60° C. for 5 minutes in the presence of a copper salt and potassium carbonate. This method has been actually applied to prostaglandin derivative tracers, and its usefulness has already been proved, such as successful imaging of prostaglandin receptors in the human brain.

The inventors also have developed a method for rapidly cross-coupling methyl iodide and a large excess of alkenyl stannane or alkynyl stannane (Patent Document 1 and Non-Patent Documents 1 and 2). The inventors also have succeeded in achieving a rapid methylation reaction using an organoboron compound (Patent Document 2).

These Pd(O)-mediated, cross-coupling reactions between $sp^3$ and $sp^2$ hybrid orbital carbon atoms or between $sp^3$ and sp hybrid orbital carbon atoms well proceed in DMF at 60° C. within 5 minutes to give the corresponding methylated products in high yield (Non-Patent Documents 3 and 4). In fact, 15R-[$^{11}$C]TIC methyl ester, which is a high-functional prostaglandin probe, has been synthesized (85% in HPLC analytical yield) using the $sp^3$-$sp^2$ (aryl) cross-coupling of these techniques, and imaging of a new prostacyclin receptor (IP$_2$) expressed in the central nervous system has been achieved by intravenous injection of the ester into living monkey and human (Non-Patent Documents 5 to 7).

Besides the above, there are some reports on Stille coupling reaction, as set forth below, in connection with the invention (Non-Patent Documents 8 to 15).

Non-Patent Document 1: M. Suzuki, H. Doi, M. Bjorkman, Y. Anderson, B. Langstrom, Y. Watanabe and R. Noyori, Chem. Eur. J., 1997, 3 (12), 2039-2042

Non-Patent Document 2: T. Hosoya, K. Sumi, H. Doi and M. Suzuki, Org. Biomol. Chem., 2006, 4, 410. 415

Non-Patent Document 3: $^{11}$C-labeled PGF$_2$ analogue of [p-$^{11}$C-methyl]MADAM: J. Tarkiainen, J. Vercouillie, P. Emond, J. Sandell, J. Hiltunen, Y. Frangin, D. Guilloteau and C. Halldin, J. Labelled Compd. Radiopharm., 2001, 44, 1013. 1023

Non-Patent Document 4: [$^{11}$C]celecoxib for imaging COX-2 expression: J. Prabhakaran, V. J. Maio, N. R. Simpson, R. L. V. Heertum, J. J. Mann, J. S. D. Kumar, J. Labelled Compds. Radiopharm. 2005, 48, 887.895.

Non-Patent Document 5: M. Suzuki, R. Noyori, B. Langstrom and Y. Watanabe, Bull. Chem. Soc. Jpn., 2000, 73, 1053. 1070

Non-Patent Document 6: M. Suzuki, H. Doi, T. Hosoya, B. Langstrom and Y. Watanabe, Trends Anal. Chem., 2004, 23, 595. 607

Non-Patent Document 7: R. Noyori, Angew. Chem., Int. Ed. Engl., 2002, 41, 2008. 2022.

Non-Patent Document 8: T. Hosoya, M. Wakao, Y. Kondo, H. Doi, M. Suzuki, "Rapid methylation of terminal acetylenes by the Stille coupling of methyl iodide with alkynyltributylstannanes: a general protocol potentially useful for the synthesis of short-lived $^{11}CH_3$-labeled PET tracers with 1-propynyl group", Org. Biomol. Chem., 2, 24-27 (2004).

Non-Patent Document 9: J. Sandell, M. Yu, P. Emond, L. Garreau, S. Chalon, K. Nagren, D. Guilloteau and C. Halldin, Bioorg. Med. Chem. Lett., 12, 3611-3613 (2002).

Non-Patent Document 10: Iida, M. Ogawa, M. Ueda, A. Tominaga, H. Kawashima, Y. Magata, S. Nishiyama, H. Tsukada, T. Mukai and H. Saji, J. Nucl. Med., 45, 878-884 (2004).

Non-Patent Document 11: Y. Huang, R. Narendran, F. Bischoff, N. Guo, Z. Zhu, S.-A Bae, A. S. Lesage and M. Laruelle, J. Med. Chem., 48, 5096-5099 (2005).

Non-Patent Document 12: I. Bennacef, C. Perrio, M. C. Lasne, L. Barre, J. Org. Chem. 72, 2161-2165, (2007).

Non-Patent Document 13: K. Menzel and G. C. Fu, J. Am. Chem. Soc., 2003, 125, 3718-3719

Non-Patent Document 14: H. Tang, K. Menzel and G. C. Fu, Angew, Int. Ed. Engl., 2003, 42, 5079-5082

Non-Patent Document 15: J. Baldwin et al, Angew. Chem. Int. Ed., 2004, 43, 1132-1136

Patent Document 1: WO/02007/046258

Patent Document 2: WO/2008/023780

DISCLOSURE OF THE INVENTION

Problems to be Solved by the Invention

A large number of drugs contain a heteroaromatic ring. For the production of heteroaromatic ring-containing tracers for use in PET etc., therefore, there has been a demand for rapid and high-yield introduction of a methyl group into a heteroaromatic ring. Unfortunately, in the conventional methylation methods using a palladium complex, no reaction conditions generally available for methylation of a heteroaromatic ring have been found yet.

An object of the present invention, which has been accomplished in view of the above circumstances, is to provide a method that enables rapid and high-yield methylation of heteroaromatic arene.

Means for Solving the Problems

The inventors attempted to apply the method of Patent Document 1, which was a method previously developed by us for rapid cross-coupling of methyl iodide with a large excess of alkenyltrialkylstannane, to rapid methylation of a heteroaromatic arene, specifically, heteroaromatic aryltrialkylstannane. However, no satisfactory result was obtained in the methylation of the heteroaromatic aryl group even under conditions where rapid methylation of an alkenyl group proceeded in high yield. As a result of further studies, the invention has been accomplished based on the finding that using an aprotic lactam as a reaction solvent enables rapid and high-yield methylation.

Thus, the invention is directed to a method for rapidly methylating a heteroaromatic arene, which includes cross-coupling methyl iodide with heteroaromatic aryltrialkylstannane in an aprotic lactam in the presence of a palladium complex, a phosphine ligand, cuprous halide, and a carbonate and/or an alkali metal fluoride.

When the method of the invention is used, Stille coupling reaction smoothly proceeds between the "$sp^2$ hybrid orbital carbon of a heteroaromatic arene" and the "$sp^3$ hybrid orbital carbon of a methyl group," so that methyl heteroaromatic arene in which the methyl group is bonded to the heteroaromatic aryl group can be rapidly obtained in high yield. This reaction is presumed to proceed through the mechanism described below.

Specifically, a sterically bulky phosphine ligand is first unsaturatedly coordinated to a zero-valent palladium complex so that an active reaction field is formed. The phosphine ligand-coordinated palladium complex is then allowed to react with methyl iodide to form a divalent palladium complex in which the phosphine ligand is coordinated to $CH_3PdI$. For oxidative addition of $CH_3I$, the palladium complex is preferably zero-valent so that it can be in an electron-rich state. Therefore, a method of performing the reaction using a zero-valent palladium complex is advantageous. Alternatively, however, a method of using a divalent palladium complex to reduce the reaction system to a zero-valent state may be used, or a method of directly using a divalent palladium complex to start the reaction (in this case, the divalent palladium complex is considered to be converted to a tetravalent palladium complex) may also be used.

On the other hand, the heteroaromatic aryltrialkylstannane is subjected to transmetalation with cuprous halide to form a highly-nucleophilic, heteroaromatic aryl copper compound. Trialkylstannyl halide, which is a by-product formed in this process, is removed from the reaction system by neutralization or precipitation reaction with a carbonate or an alkali metal fluoride (the carbonate forms trialkylstannyl carbonate, and the alkali metal fluoride forms trialkylstannyl fluoride as a precipitate). Such Cu/carbonate and Cu/alkali metal fluoride have a synergistic effect to accelerate the transmetalation from Sn to Cu.

The divalent palladium complex produced as described above in which the phosphine ligand is coordinated to $CH_3PdI$ is then subjected to substitution reaction with the heteroaromatic aryl copper compound, so that a complex is formed in which the phosphine ligand is coordinated to $CH_3PdR$ (wherein R represents a heteroaromatic aryl group), and the complex is further subjected to reductive elimination, so that a methylated heteroaromatic arene is produced.

In the rapid methylation of heteroaromatic arene according to the present invention, the solvent plays a very important role. Specifically, the inventors performed the reaction in various solvents such as 1,3-dimethylimidazolidine-2-one (DMI), dimethylformamide (DMF), N,N-dimethylacetamide (DMA), dimethylsulfoxide (DMSO), hexamethylphosphoric triamide (HMPA), THF, and toluene, but the yield was low in all cases. In contrast, when an aprotic lactam was used as the solvent, the yield dramatically increased, and the reaction proceeded in a short time. As used herein, the term "aprotic lactam" refers to a cyclic amide (namely, lactam) having no hydrogen atom directly bonded to the nitrogen atom. While it is not clear why the yield dramatically increases when such an aprotic lactam is used as a solvent, the following two reasons are considered: 1) the lone-pair electrons of the aprotic lactam are coordinated to the unoccupied orbitals of the palladium atom in a palladium complex, which is produced in the course of the reaction, so that the instability of the orbitals is reduced, which can minimize side reactions such as decomposition; 2) when the heteroaromatic arene has a basic nitrogen atom like pyridine or a pyridine derivative, the lone-pair electrons on the basic nitrogen atom is coordinated to the palladium or copper element, so that the reactivity of the tin substrate decreases, but this coordination competes with the coordination of the lactam, which has strong coordinating power, to the metal, so that the tin substrate is reproduced with sufficient reactivity.

Therefore, the method for rapidly methylating heteroaromatic arene according to the present invention enables rapid and high-yield methylation of heteroaromatic arene.

The number of carbon atoms in the alkyl moiety of the heteroaromatic aryltrialkylstannane is preferably, but not limited to, 1 to 10, more preferably 1 to 6. The alkyl group may be a straight or branched chain. The heteroaromatic aryl group and the alkyl group may each have a substituent.

The aprotic lactam is preferably N-alkyl-2-pyrrolidinone. The inventors have demonstrated that using N-methyl-2-pyrrolidinone, one of N-alkyl-2-pyrrolidinone species, ensures rapid and high-yield methylation of heteroaromatic arene. The alkyl group of N-alkyl-2-pyrrolidinone preferably has 1 to 6 carbon atoms, more preferably 1 to 3 carbon atoms.

The carbonate for use as a scavenger in an embodiment of the invention may be an alkali carbonate salt such as potassium carbonate, sodium carbonate, cesium carbonate, lithium carbonate, or calcium carbonate. However, potassium carbonate is particularly preferred. If an appropriate carbonate is selected depending on the type of heteroaromatic aryltrialkylstannane as a substrate, the desired compound can be obtained in higher yield.

The alkali metal fluoride for use in an embodiment of the invention may be any of sodium fluoride, potassium fluoride, and cesium fluoride. Cesium fluoride is particularly preferred. The cesium ion has a relatively large ionic radius so that the fluoride ion can have high solubility and nucleophilicity, which allows more rapid production of trialkylstannyl fluoride. Therefore, the transmetalation from Sn to Cu is accelerated, so that the reaction is entirely further accelerated.

The bulky phosphine ligand is preferable. Tri-o-tolylphosphine may be used as such a phosphine ligand. The inventors have demonstrated that when this phosphine ligand is used, methyl alkene is rapidly obtained in high yield. This may be because tri-o-tolylphosphine is so bulky as to form a highly-active reaction field. Tri-o-tolylphosphine also has the advantage that it is a stable crystalline compound in the air and therefore easy to handle. For example, other bulky phosphine ligands include (di-tert-butyl)methylphosphine.

The cuprous halide, which is added in the method for rapidly methylating heteroaromatic arene according to the present invention, may be any one of cuprous bromide and cuprous chloride. Transmetalation between the cuprous halide and the heteroaromatic aryltrialkylstannane produces a highly-nucleophilic heteroaromatic aryl copper compound, which achieves a high, reaction-accelerating effect.

Not only methyl iodide labeled with $^{11}C$ but also methyl iodide labeled with any one of $^{12}C$, $^{13}C$, $^{14}C$, and $CD_3$ may be used in the method for rapidly methylating heteroaromatic arene according to the present invention. The labeled methyl iodide can be effectively used to form a tracer for use in kinetic analysis of candidate compounds for drug discovery by PET method or the like, a tracer for use in disease diagnosis methods, a tracer for use in drug metabolism studies, or a tracer for use in research and development of new drugs.

The method for rapidly methylating heteroaromatic arene according to the present invention may be performed using a two-step synthesis method, which includes performing the synthesis of a methyl palladium complex and the Sn/Cu transmetalation reaction in different reaction vessels, respectively, and then mixing the different reaction liquids. Specifically, the method for rapidly methylating heteroaromatic arene includes: a step of preparing a palladium complex including allowing a methyl iodide, a palladium complex, and a phosphine ligand to react together in an aprotic lactam to prepare a $CH_3PdI$ complex solution; a step of preparing an aryl copper including allowing to react in an aprotic lactam in the presence of a heteroaromatic aryltrialkylstannane, a cuprous halide, and a carbonate and/or an alkali metal fluoride to prepare a heteroaromatic aryl copper solution; and a step of methylating including mixing the $CH_3PdI$ complex solution with the heteroaromatic aryl copper solution to form a methylated heteroaromatic arene.

The cuprous halide may become a catalyst poison in the step of preparing a palladium complex including allowing a methyl iodide, a palladium complex, and a phosphine ligand to react together in an aprotic lactam to form a $CH_3PdI$ complex solution. Therefore, a two-step synthesis method, which includes: a step of preparing a palladium complex including allowing a methyl iodide, a palladium complex, and a phosphine ligand to react together in an aprotic lactam to form a $CH_3PdI$ complex solution; and a step of preparing an aryl copper including allowing to react in an aprotic lactam in the presence of a heteroaromatic aryltrialkylstannane, a cuprous halide, and a carbonate and/or an alkali metal fluoride to prepare a heteroaromatic aryl copper solution, is performed in such a manner that the step of preparing a palladium complex and the step of preparing an aryl copper are performed in different vessels, respectively, so that the catalyst-poison effect of the cuprous halide can be minimized. This makes it possible to perform rapid methylation of heteroaromatic aryltrialkylstannane in a higher yield than that obtained when the reactions are performed in a single reaction vessel.

The molar ratio of the phosphine ligand to the palladium complex is preferably 4 or more, in particular, preferably 8 to 32. According to the result of tests performed by the inventors, a high yield is achieved when the molar ratio of the phosphine ligand to the palladium complex is 4 or more (in particular, from 8 to 32). This may be because like the function of the lactam with strong coordinating power, the coordinating power of the phosphine ligand to the palladium and copper elements works to reproduce the tin substrate from the metal/tin substrate complex to which the nitrogen atom is temporarily coordinated.

Reagents for use in the method for rapidly methylating heteroaromatic arene according to the present invention may be previously mixed to form a kit. An aprotic lactam may be added to the kit, and methyl iodide may be further introduced thereto so that a methylated heteroaromatic arene can be synthesized. In other words, there is provided a PET tracer preparation kit, which includes a mixture of a palladium complex, a phosphine ligand, heteroaromatic aryltrialkylstannane, cuprous halide, and a carbonate and/or an alkali metal fluoride. When such a PET tracer preparation kit is provided, a PET tracer can be very simply synthesized only by adding an aprotic lactam to the kit and introducing methyl iodide into the kit. The kit preferably further includes a column for separating methyl alkene from the reaction liquid. In this case, there is no need to prepare an additional separation column, so that a highly-convenient, PET tracer preparation kit is provided.

The kit also preferably includes, separately, a first mixture of the palladium complex and the phosphine ligand, and a second mixture of a heteroaromatic aryltrialkylstannane, a cuprous halide, and a carbonate and/or a alkali metal fluoride. In this case, the synthesis of the methyl palladium complex and the Sn/Cu transmetalation can be performed in different reaction vessels, respectively, and then the respective reaction liquids can be mixed. This makes it possible to minimize the effect of the cuprous halide as a catalyst poison. In this case, therefore, rapid methylation of heteroaromatic aryltrialkylstannane can be performed with a higher yield than that obtained in the case where the reaction is performed in a single reaction vessel.

BRIEF DESCRIPTION OF THE DRAWINGS

The FIGURE shows the results of the synthesis of $^{11}$C-labeled 3-picoline and 2-picoline.

BEST MODE FOR CARRYING OUT THE INVENTION

The method for rapidly methylating a heteroaromatic arene according to the invention is presumed to have the following reaction mechanism (hereinafter, rapid methylation of pyridine will be described as an example).

[Chemical Formula 1]

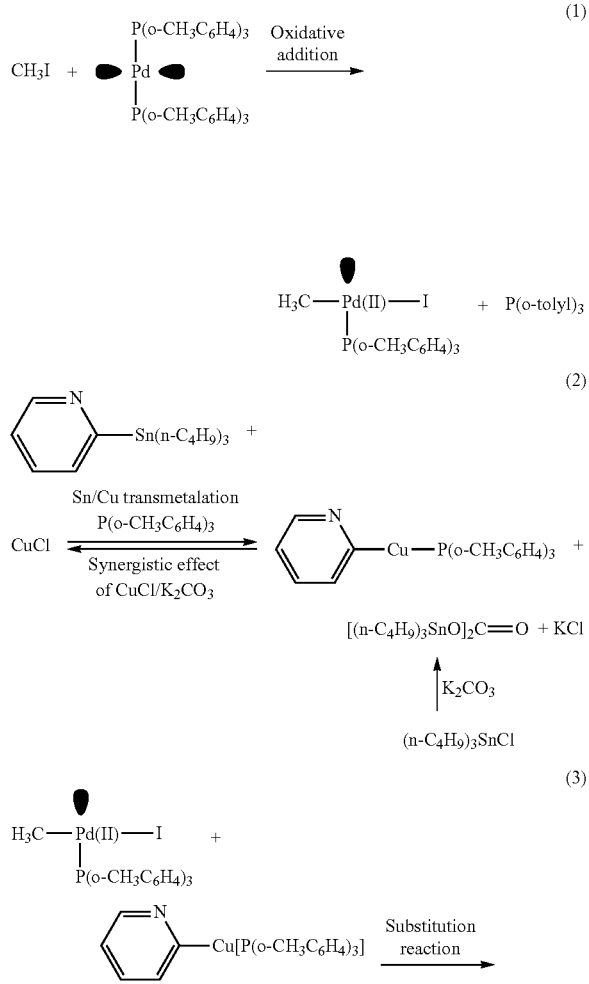

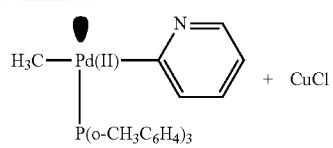

Specifically, a sterically bulky phosphine ligand (o-tolylphosphine in Chemical Formula 1) is first unsaturatedly coordinated to a zero-valent palladium complex so that an active reaction field is formed, and as shown in Formula (1), the phosphine ligand-coordinated palladium complex is allowed to react with methyl iodide to form a divalent palladium complex in which the phosphine ligand is coordinated to $CH_3PdI$.

On the other hand, as shown in Formula (2), the heteroaromatic aryl (a pyridyl group in Chemical Formula 1) trialkylstannane is subjected to transmetalation with cuprous halide (cuprous chloride in Chemical Formula 1) to form a highly-nucleophilic, heteroaromatic aryl (pyridine in Chemical Formula 1) copper compound. Trialkylstannyl chloride, which is a by-product formed in this process, is removed from the reaction system by neutralization or precipitation reaction with a carbonate or an alkali metal fluoride (the carbonate forms trialkylstannyl carbonate, and the alkali metal fluoride forms trialkylstannyl fluoride as a precipitate). Such Cu/carbonate and Cu/alkali metal fluoride have a synergistic effect to accelerate the transmetalation from Sn to Cu.

The divalent palladium complex produced according to Formula (1) in which the phosphine ligand is coordinated to $CH_3PdI$ is then subjected to substitution reaction with the heteroaromatic aryl (a pyridyl group in the Formula) copper compound, so that a complex is formed in which the phosphine ligand is coordinated to $CH_3PdR$ (wherein R represents a pyridyl group) (Formula (3)), and the complex is further subjected to reductive elimination, so that a methylated heteroaromatic arene (pyridine in the Formula) is produced (Formula (4)).

Hereinafter, examples of embodiment of the invention will be described in detail. In the description below, $Pd_2(dba)_3$ and $P(o\text{-tolyl})_3$ represent tris(dibenzylideneacetone)dipalladium and tri-o-tolylphosphine, respectively.

The nine heteroaromatic aryltributylstannanes 1a to 1i shown in Table 1 were selected as substrates to be subjected to rapid methylation. Methylation was attempted using each of the methods of Example 1 and Comparative Examples 1 to 3, in which the molar ratio of methyl iodide to the tin substrate (used in a large excess) was 1:40. The heteroaromatic aryltributylstannane was used in a large excess, bearing in mind that in practical synthesis of PET tracers, a tiny amount of $^{11}$C-labeled $CH_3I$ synthesized in a synchrotron is allowed to react with heteroaromatic aryltributylstannane.

TABLE 1
Rapid methyl iodide-trapping reaction of heteroaromatic stannane
| Entry | Heteroaromatic stannane | Methylated product | Yield [%]<sup>1),2)</sup> Methylation method ||||
|---|---|---|---|---|---|---|
| | | | A*<sup>1</sup> | B*<sup>2</sup> | C*<sup>3</sup> | D*<sup>4</sup> |
| 1 | 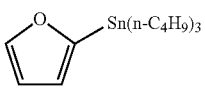 1a | 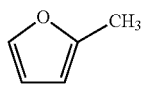 2a | 28 | 75 | 73 | 80 |
| 2 | 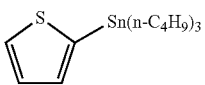 1b | 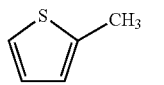 2b | 57 | 87 | 91 | 94 |
| 3 | 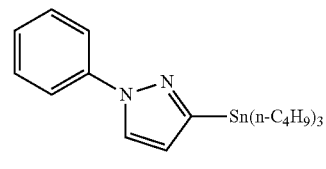 1c | 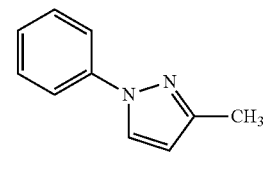 2c | 52 | 88 | 90 | 94 |
| 4 | 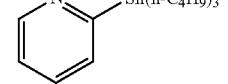 1d | 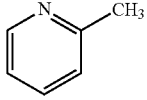 2d | 16 (14)<sup>3)</sup> | 67 | 63 | 81 |
| 5 | 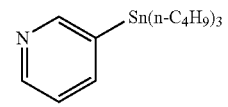 1e | 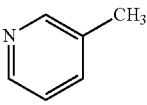 2e | 25 (53)<sup>4)</sup> | 61 | 66 | 80 |
| 6 | 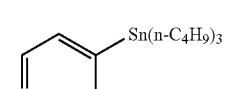 1f | 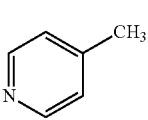 2f | 79 | 60 | 68 | 87 |
| 7 | 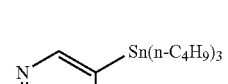 1g | 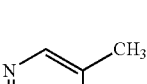 2g | 3 | 50 | 48 | 62 (87)<sup>5)</sup> |
| 8 | 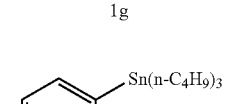 1h | 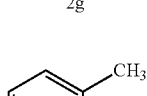 2h | 25 | 72 | 70 | 90 |

TABLE 1-continued

Rapid methyl iodide-trapping reaction of heteroaromatic stannane

| Entry | Heteroaromatic stannane | Methylated product | Yield [%][1),2)] Methylation method | | | |
|---|---|---|---|---|---|---|
| | | | A*[1] | B*[2] | C*[3] | D*[4] |
| 9 | 1i (isoquinolin-4-yl-Sn(n-C$_4$H$_9$)$_3$) | 2i (4-methylisoquinoline) | 12 | 83 | 75 | 83 |

*[1]A: Comparative Example 1,
*[2]B: Comparative Example 2
*[3]C: Comparative Example 3,
*[4]D: Example 1
[1)]A single product was identified by comparison with a standard sample in GLC analysis.
[2)]The yield was determined based on the amount of consumption of CH$_3$I by GLC analysis using n-nonane or n-heptane as an internal standard substance (the average of two or three measurements).
[3)]CH$_3$I/stannane/Pd$_2$(dba)$_3$/P(o-tolyl)$_3$/CuCl/K$_2$CO$_3$ (1:40:0.5:2:2:2) were heated in DMF at 80° C. for 3 minutes (the method of Laruelle et al. in Non-Patent Document 12).
[4)]CH$_3$I/stannane/Pd$_2$(dba)$_3$/P(o-tolyl)$_3$/ (1:40:0.5:2) were heated in DMF at 120° C. for 5 minutes (the method of Saji et al. in Non-Patent Document 11).
[5)]The reaction was performed at 100° C.

METHOD OF EXAMPLE 1

In the method of Example 1, heteroaromatic aryltrialkylstannanes 1a to 1i were methylated as described below (these are named Examples 1a to 1i, respectively). The respective reagents were added in the following molar ratio: CH$_3$I:stannane:Pd$_2$(dba)$_3$:P(o-tolyl)$_3$:CuBr:CsF=1:40:0.5:16:2:5. Specifically, under an argon atmosphere, Pd$_2$(dba)$_3$ (4.6 mg, 5.0 µmol), P(o-tolyl)$_3$ (48.8 mg, 160 µmol), CuBr (20 µmol), and CsF (50 µmol) were weighed into a 10 mL Schlenk tube, and NMP (0.5 mL) was added thereto and stirred at room temperature for 5 minutes. Subsequently, an NMP (0.5 mL) solution of one of heteroaromatic aryltrialkylstannanes 1a to 1i (400 µmol) and an NMP solution of CH$_3$I (10 µmol of 12.5 µmol/0.80 M) were sequentially added, and the mixture was stirred at 60° C. for 5 minutes. After the reaction, the mixture was quickly cooled in an ice bath, and diethyl ether (1 mL) was added thereto. The mixture was loaded on a short column of silica-gel (0.5 g) and eluted with diethyl ether (1 mL). Subsequently, GLC analysis was performed with n-nonane (50 µmol of a 50 µL/0.10 M NMP solution) added as an internal standard.

METHOD OF COMPARATIVE EXAMPLE 1

In the method of Comparative Example 1, heteroaromatic aryltrialkylstannanes 1a to 1i were methylated as described below (these are named Comparative Examples 1a to 1i, respectively). The respective reagents were added in the following molar ratio: CH$_3$I:stannane:Pd$_2$(dba)$_3$:P(o-tolyl)$_3$:CuCl:K$_2$CO$_3$=1:40:0.5:16:2:5. The specific procedure was as follows. Under an argon atmosphere, Pd$_2$(dba)$_3$ (4.6 mg, 5.0 µmol), P(o-tolyl)$_3$ (6.1 mg, 20 µmol), CuCl (2.9 mg, 20 µmol), and K$_2$CO$_3$ (7.0 mg, 50 µmol) were weighed into a 10 mL Schlenk tube, and DMF (0.5 mL) was added thereto and stirred at room temperature for 5 minutes. Subsequently, a DMF (0.5 mL) solution of one of heteroaromatic aryltrialkylstannanes 1a to 1i (400 µmol) and a DMF solution of CH$_3$I (10 µmol of 12.5 µmol/0.80 M) were sequentially added, and the mixture was stirred at 60° C. for 5 minutes. After the reaction, the mixture was quickly cooled in an ice bath, and diethyl ether (1 mL) was added thereto. The mixture was loaded on a short silica-gel (0.5 g) column and eluted with diethyl ether (1 mL). Subsequently, GLC analysis was performed with n-nonane (50 µmol of a 50 µL/0.10 M DMF solution) added as an internal standard.

The above procedure was used except that as for 3) in the table, CH$_3$I:stannane:Pd$_2$(dba)$_3$:P(o-tolyl)$_3$:CuCl:K$_2$CO$_3$=1:40:0.5:2:2:2 were heated in DMF at 80° C. for 3 minutes (the method of Laruelle et al. in Non-Patent Document 12) and that as for 4) in the table, CH$_3$I:stannane:Pd$_2$(dba)$_3$:P(o-tolyl)$_3$=1:40:0.5:2 were heated in DMF at 120° C. for 5 minutes (the gradual process of Saji et al. in Non-Patent Document 11).

METHOD OF COMPARATIVE EXAMPLE 2

In the method of Comparative Example 2, heteroaromatic aryltrialkylstannanes 1a to 1i were methylated as in Comparative Example 1, except that P(o-tolyl)$_3$ was added in a large excess, as much as 8 times the amount in Comparative Example 1 (these are named Comparative Examples 2a to 2i, respectively). The respective reagents were added in the following molar ratio:

CH$_3$I:stannane:Pd$_2$(dba)$_3$:P(o-tolyl)$_3$:CuCl:K$_2$CO$_3$=1:40:0.5:16:2:5.

METHOD OF COMPARATIVE EXAMPLE 3

In the method of Comparative Example 3, heteroaromatic aryltrialkylstannanes 1a to 1i were methylated as in Comparative Example 2, except that a combination of CuBr/CsF was used in place of CuCl/K$_2$CO$_3$ (these are named Comparative Examples 3a to 3i, respectively). The respective reagents were added in the following molar ratio: CH$_3$I:stannane:Pd$_2$(dba)$_3$:P(o-tolyl)$_3$:CuBr:CsF=1:40:0.5:16:2:5.

<Results>

The method of Comparative Example 1, which uses P(o-tolyl)₃, a bulky ligand, has been demonstrated to methylate, in very high yield, non-hetero aromatic aryltrialkylstannane or alkenyltrialkylstannane (see for example Patent Document 1 and Non-Patent Document 1). The methods of Comparative Examples 2 and 3 are improved versions of the method of Comparative Example 1, with which higher yield can be expected for aromatic aryltrialkylstannane and alkenyltrialkylstannane (see Patent Document 1).

As shown in Table 1, however, the methylation method of Comparative Example 1 provided low yields with respect to all the aromatic aryltrialkylstannanes.

In the method of Comparative Example 2 where P(o-tolyl)₃ was added in a large excess as much as 8 times the amount in Comparative Example 1, the yield was still not sufficient, although it was effective in improving the yield.

Also in Comparative Example 3 where the copper halide was changed to cuprous bromide and CsF with a high scavenger effect was used in place of $K_2CO_3$, the yield was not sufficient with respect to the heteroaromatic aryltrialkylstannanes excluding 1b and 1c, although the effect of improving the yield was observed.

In contrast, the method of Example 1, in which N-methyl-2-pyrrolidinone (NMP) was used as a solvent in place of dimethylformamide (DMF), achieved high-yield methylation of all of heteroaromatic aryltrialkylstannanes 1a to 1i and was found to be usable as a general method for methylating heteroaromatic arene.

EXAMPLE 2 AND COMPARATIVE EXAMPLES 5 TO 11

In order to study whether changing the solvent makes a difference in reactivity, the methylation reaction of tributyl (2-pyridyl)stannane (1d) (see Chemical Formula 2) was performed using different solvents. Specifically, N-methyl-2-pyrrolidinone (NMP) was used in Example 2, dimethylformamide (DMF) in Comparative Example 5, N,N-dimethylacetamide (DMA) in Comparative Example 6, 1,3-dimethylimidazolidine-2-one (DMI) in Comparative Example 7, toluene in Comparative Example 8, tetrahydrofuran (THF) in Comparative Example 9, dimethylsulfoxide (DMSO) in Comparative Example 10, and hexamethylphosphoric triamide (HMPA) in Comparative Example 11. The reagents were added in the ratio shown below, and the specific experimental procedure was the same as in Example 1.
$CH_3I:1d:Pd_2(dba)_3:P(o-tolyl)_3:CuBr:CsF=1:40:0.5:16:2:5.$

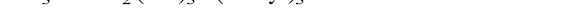

[Chemical Formula 2]

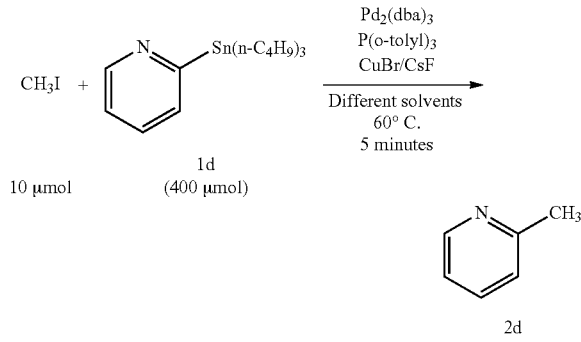

As a result, as shown in Table 2, the methylation proceeded in a significantly higher yield when NMP was used as a solvent than when the other aprotic polar solvents were used.

TABLE 2

|  | Solvent | Yield (%) |
|---|---|---|
| Example 2 | NMP | 81 |
| Comparative Example 5 | DMF | 65 |
| Comparative Example 6 | DMA | 69 |
| Comparative Example 7 | DMI | 18 |
| Comparative Example 8 | Toluene | 20 |
| Comparative Example 9 | THF | 38 |
| Comparative Example 10 | DMSO | 23 |
| Comparative Example 11 | HMPA | 34 |

EXAMPLE 3

In Example 3, CuCl and $K_2CO_3$ were used in place of CuBr and CsF, respectively, which were used in Example 2. The other reaction conditions were the same as those in Example 2, and a description thereof is omitted here. As a result, 2-methylpyridine (2d) was obtained in a yield of 66%, and the method was found to be usable as a rapid methylation technique. It was also found that as for a combination of a copper halide salt and a scavenger salt, a combination of CuBr—CsF was more preferable than a combination of CuCl—$K_2CO_3$.

Examples 4 to 7 described below are applications of the ¹¹C-labeled methylation using ¹¹C methyl iodide as a starting material. Examples 4 to 6 are each an example of a method for rapidly methylating heteroaromatic arene using a two-pot process, which includes providing two reaction vessels, performing a process of preparing a palladium complex in the first reaction vessel, performing a process of preparing heteroaromatic aryl copper in the second reaction vessel, and performing a methylation process in which the resulting $CH_3PdI$ complex solution and the resulting heteroaromatic aryl copper solution are mixed to form a methylated heteroaromatic arene. Example 7 is an example of a method for rapidly methylating heteroaromatic arene using a one-pot process in which the reaction process is performed in a single reaction vessel.

EXAMPLE 4

Synthesis of 3-[¹¹C]picoline Using CuBr and CsF

An NMP solution (0.27 mL) of trisdibenzylideneacetone dipalladium (2.5 mg, 2.7 µmol) and tri-o-tolylphosphine (13 mg, 44 µmol) was prepared in a reaction vessel (A) and kept at room temperature. The solution was prepared in the reaction vessel (A) 10 to 20 minutes before [¹¹C] methyl iodide was blown into the vessel.

An NMP solution (60 mL) of (3-pyridinyl)tributylstannane (3.0 mg, 8.1 µmol) as a tin precursor, CuBr (0.78 mg, 5.4 µmol), and CsF (2.1 mg, 14 µmol) was prepared in a reaction vessel (B) and kept at room temperature. Subsequently, [¹¹C] methyl iodide was blown at a gas flow rate of 60-80 mL/min into the reaction vessel (A), and then the mixture was allowed to stand for 1 minute. The resulting solution was transferred to the reaction vessel (B). The mixed solution in the reaction vessel (B) was heated at 60° C. for 5 minutes. The resulting reaction solution was diluted with 2 mL of acetonitrile and then filtered through a cotton plug. The filtrate was subjected to HPLC, and the HPLC analytical yield of the labeled compound was calculated. HPLC analytical yield: 91.4%.

The HPLC analytical conditions were as follows.
Column: NACALAI TESQUE, INC., COSMOSIL, C18-MS-II, 4.6 mm I.D.–150 mm, 5 mm
Mobile phase: $CH_3CN:H_2O=25:75$
Flow rate: 1 mL/min
Detection wavelength: 254 nm
Retention time: 4.6 min.

The result of the HPLC analysis of the reaction yield is shown in the FIGURE.

EXAMPLE 5

Synthesis of 3-[$^{11}$C]picoline Using CuCl and $K_2CO_3$

An NMP solution (0.27 mL) of trisdibenzylideneacetone dipalladium (2.5 mg, 2.7 µmol) and tri-o-tolylphosphine (13 mg, 44 µmol) was prepared in a reaction vessel (A) and kept at room temperature. The solution was prepared in the reaction vessel (A) 10 to 20 minutes before [$^{11}$C]methyl iodide was blown into the vessel.

On the other hand, an NMP solution (60 mL) of (3-pyridinyl)tributylstannane (3.0 mg, 8.1 µmol) as a tin precursor, CuCl (0.54 mg, 5.4 µmol), and $K_2CO_3$ (1.9 mg, 14 µmol) was prepared in a reaction vessel (B) and kept at room temperature. Subsequently, [$^{11}$C]methyl iodide was blown at a gas flow rate of 60-80 mL/min into the reaction vessel (A), and then the mixture was allowed to stand for 1 minute. The resulting solution was transferred to the reaction vessel (B). The mixed solution in the reaction vessel (B) was heated at 60° C. for 5 minutes. The resulting reaction solution was diluted with 2 mL of acetonitrile and then filtered through a cotton plug. The filtrate was subjected to HPLC, and the HPLC analytical yield of the labeled compound was calculated. HPLC analytical yield: 91.3%. The HPLC analytical conditions were as follows.
Column: NACALAI TESQUE, INC., COSMOSIL, C18-MS-II, 4.6 mm I.D.—150 mm, 5 mm
Mobile phase: $CH_3CN:H_2O=25:75$
Flow rate: 1 mL/min
Detection wavelength: 254 nm
Retention time: 4.6 min.

The result of the HPLC analysis of the reaction yield is shown in the FIGURE. The reaction proceeded even at 100° C., and the desired 3-[$^{11}$C]picoline was obtained in an HPLC analytical yield of 95.2%.

EXAMPLE 6

Synthesis of 2-[$^{11}$C]picoline

The synthesis of 2-[$^{11}$C]picoline was performed using (2-pyridinyl)tributylstannane as a tin precursor according to the method of synthesizing 3-[$^{11}$C]picoline with CuCl and $K_2CO_3$ described in Example 5. HPLC analytical yield: 98.9%. The HPLC analytical conditions were as follows.
Column: NACALAI TESQUE, INC., COSMOSIL, C18-MS-II, 4.6 mm I.D.–150 mm, 5 mm
Mobile phase: $CH_3CN:H_2O=20:80$
Flow rate: 1 mL/min
Detection wavelength: 254 nm
Retention time: 4.9 min.

The result of the HPLC analysis of the reaction yield is shown in the FIGURE.

EXAMPLE 7

An NMP (0.4 ml) solution of tributyl(2-pyridyl)stannane (1d) (4.5 µmol), $Pd_2(dba)_3$ (1.8 mg, 1.97 µmol), P(o-tolyl)$_3$ (19.2 mg, 63.2 µmol), CuBr (20 µmol), and CsF (2.100 µmol) is prepared in a 1.0 ml reaction vessel and kept at room temperature. Subsequently, $^{11}$C-labeled methyl iodide is trapped into the solution at room temperature, and the mixture is allowed to stand for 1 minute. The $^{11}$C is produced by $^{14}$N(p,α)$^{11}$C nuclear reaction using CYPRIS HM-12S Cyclotron manufactured by Sumitomo Heavy Industries, Ltd. Using a $^{11}$C methyl iodide automatic synthesizer, $^{11}CO_2$ gas as a starting material is then converted in order of $CO_2 \rightarrow CH_3OH \rightarrow CH_3I$. After the resulting mixed solution is heated at 65° C. for 5 minutes, the reaction solution is filtered through a cotton plug using a $NMP:H_2O$ (1:5) solution (300 µl) (or may be filtered through an SPE solid phase column). The filtrate is subjected to HPLC. The desired $^{11}$C-labeled methylated product is concentrated with an evaporator and then used to form a specific clinical administration solution.
<Equipment, Methods, and Reagents Used in the Experiments>

The analytical gas chromatography (GC) was performed using FID detector-equipped GC-2010 and GC-17A manufactured by Shimadzu Corporation. Helium and nitrogen were used as carrier gases. The capillary columns used were TC-1701 (60 m, 0.25 mm i.d., df=0.25 mm) manufactured by GL Science Inc. and CP-Volamine (60 m×0.32 mm i.d.) manufactured by GL Science Inc. The $^{11}$C was produced by $^{14}$N (p, α) $^{11}$C nuclear reaction using CYPRIS HM-12S Cyclotron manufactured by Sumitomo Heavy Industries, Ltd. A series of procedures including heating and dilution of the reaction solution, injection into the high performance liquid chromatography (HPLC) system, preparative separation, concentration, and sterilization were performed using an originally-developed automatic synthesizer. HPLC was performed using a multi-UV detector SPD-20AC, a column oven CTO-20-AC, a liquid feed pump LC-20AB, a system controller CBM-20A, and an auto-sampler SIL-20A all manufactured by Shimadzu Corporation. The emitted radioactivity was measured using RLC-700 Radioanalyzer manufactured by ALOKA CO., LTD. All experimental procedures were performed under an argon stream according to the standard Schlenk technique. Each reaction solvent and solution were added to the reaction solution under an argon pressure using a gas-tight syringe or a stainless steel cannula. Commercially-available reagents were used as received, which were dehydrated N,N-dimethylformamide (DMF) (manufactured by KANTO CHEMICAL CO., INC.), dehydrated N-methyl-2-pyrrolidinone (NMP) (manufactured by KANTO CHEMICAL CO., INC.), dehydrated tetrahydrofuran (THF) (manufactured by Wako Pure Chemical Industries, Ltd.), dehydrated toluene (manufactured by Wako Pure Chemical Industries, Ltd.), tris(dibenzylideneacetone)dipalladium(0) (manufactured by Sigma-Aldrich Co.), n-nonane (manufactured by NACALAI TESQUE, INC.), 9tri-o-tolylphosphine (manufactured by Sigma-Aldrich Co.), copper chloride (manufactured by Wako Pure Chemical Industries, Ltd.), copper bromide (manufactured by Wako Pure Chemical Industries, Ltd.), potassium carbonate (manufactured by Wako Pure Chemical Industries, Ltd.), cesium fluoride (manufactured by Sigma-Aldrich Co.), 1,3-dimethylimidazolidine-2-one (DMI) (manufactured by NACALAI TESQUE, INC.), N,N-dimethylacetamide (DMA) (manufactured by KANTO CHEMICAL CO., INC.), dimethylsulfoxide (manufactured by KANTO CHEMICAL CO., INC.), hexamethylphosphoric triamide (HMPA) (manufactured by Tokyo Chemical Industry Co., Ltd.), 2,6-lutidine, triethylamine (manufactured by NACALAI TESQUE, INC.), 1,4-diazabicyclo[2.2.2]octane (DABCO) (manufactured by KANTO CHEMICAL CO., INC.), 2-(tributylstannyl)furan (manufactured by Tokyo Chemical Industry Co., Ltd.), 2-(tributylstannyl)thiophene (manufactured by Tokyo Chemical Industry Co., Ltd.), 2-(tributylstannyl)pyridine (manufactured by Tokyo Chemical Industry Co., Ltd.), 3-(tributylstannyl)pyridine (synthetic product, manufactured by Frontier Scientific, Inc.), 4-(tributylstannyl)pyridine (synthetic product), 5-bromopyrimidine, and 4-bromoisoquinoline. Distilled methyl iodide was used. 5-(tributylstannyl)pyrimidine (1 g) was prepared by cross-coupling reaction of 5-bromopyrimidine with bis(tributyltin) in the presence of a palladium(0) catalyst.

While the present invention has been described based on examples, it will be understood that the examples are not intended to limit the invention and may be altered or modified in various ways without departing from the gist of the invention. The scope of the invention also encompasses such alterations and modifications.

Industrial Applicability

The method for rapidly methylating heteroaromatic arene according to the present invention makes it possible to introduce a $^{11}C$ group label into a neutral or basic heteroaromatic ring skeleton, which has been difficult in conventional techniques. Since many biologically active substances such as inhibitors capable of controlling intracellular information transmission signals have a heteroaromatic ring, the invention provides very effective means for drug development, etc. and studies of molecular imaging of an entire living body including a human body.

The invention claimed is:

1. A method for methylating a heteroaryltrialkylstannane, comprising cross-coupling methyl iodide with the heteroaryltrialkylstannane in an aprotic lactam with the addition of a palladium complex, at least one phosphine ligand selected from the group consisting of tri-o-tolylphosphine and (di-tert-butyl)methylphosphine, a cuprous halide, and an alkali carbonate salt to obtain a methylated heteroarene; wherein the palladium complex is tris(dibenzylideneacetone)dipalladium.

2. The method according to claim 1, wherein the aprotic lactam is N-alkyl-2-pyrrolidinone.

3. The method according to claim 2, wherein the N-alkyl-2-pyrrolidinone is N-methyl-2-pyrrolidinone.

4. The method according to claim 1, wherein the alkali carbonate salt is potassium carbonate.

5. The method according to claim 1, wherein the cuprous halide is any one of cuprous bromide and cuprous chloride.

6. The method according to claim 1, wherein the methyl iodide used is labeled with any one of $^{11}C$, $^{12}C$, $^{13}C$, $^{14}C$, or deuterated methyl.

7. The method according to claim 1, wherein the molar ratio of the phosphine ligand to the palladium complex is 4 or more.

8. A method for methylating a heteroaryltrialkylstannane, comprising:
    preparing a $CH_3PdI$ complex solution by allowing a methyl iodide, a palladium complex, and at least one phosphine ligand selected from the group consisting of tri-o-tolylphosphine and (di-tert-butyl)methylphosphine to react together in an aprotic lactam;
    preparing a heteroaromatic aryl copper solution by allowing a heteroaryltrialkylstannane, a cuprous halide, and an alkali carbonate salt to react in an aprotic lactam; and
    mixing the $CH_3PdI$ complex solution with the heteroaromatic aryl copper solution to form a methylated heteroarene;
    wherein the palladium complex is tris(dibenzylideneacetone)dipalladium.

9. The method according to claim 1, wherein $^{11}C$-labeled methyl iodide is cross-coupled with a heteroaryltrialkylstannane in N-methyl-2-pyrrolidinone with the addition of the palladium complex, the phosphine ligand, cuprous bromide, and cesium fluoride, wherein the molar ratio of the phosphine ligand to the palladium complex is 4 or more.

10. The method according to claim 1, wherein the palladium complex is a zero-valent palladium complex.

\* \* \* \* \*